United States Patent
Wakamura

(10) Patent No.: US 8,030,245 B2
(45) Date of Patent: Oct. 4, 2011

(54) AGRICULTURAL CHEMICAL COMPONENT AND DECOMPOSER FOR RESIDUAL AGRICULTURAL CHEMICAL

(75) Inventor: Masato Wakamura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1459 days.

(21) Appl. No.: 11/012,103

(22) Filed: Dec. 16, 2004

(65) Prior Publication Data

US 2005/0159317 A1  Jul. 21, 2005

Related U.S. Application Data

(63) Continuation of application No. PCT/JP02/06370, filed on Jun. 25, 2002.

(51) Int. Cl.
*A01N 25/12* (2006.01)
(52) U.S. Cl. .................................................. 504/367
(58) Field of Classification Search ............... 504/367
See application file for complete search history.

(56) References Cited

U.S. PATENT DOCUMENTS

| | | | | |
|---|---|---|---|---|
| 4,272,398 A * | 6/1981 | Jaffe | .................... | 427/213.31 |
| 6,090,736 A | 7/2000 | Taoda et al. | | |
| 6,274,051 B1 * | 8/2001 | Cronce | .................... | 210/758 |
| 6,407,156 B1 | 6/2002 | Hagihara et al. | | |
| 6,589,912 B2 | 7/2003 | Kawai | | |
| 7,157,503 B2 * | 1/2007 | Wakamura | .................... | 523/122 |
| 2003/0219624 A1 * | 11/2003 | Aso et al. | .................... | 428/689 |

FOREIGN PATENT DOCUMENTS

| | | |
|---|---|---|
| JP | 7-187933 | 7/1995 |
| JP | 9-87121 A | 3/1997 |
| JP | 2000-239823 A | 9/2000 |
| JP | 2000-327315 | 11/2000 |
| JP | 2001-10914 A | 1/2001 |
| JP | 2001-302220 | 10/2001 |
| JP | 2002-172332 A | 6/2002 |

OTHER PUBLICATIONS

Japanese Office Action dated Nov. 13, 2007 issued in corresponding Japanese Application No. 2004-515467.
Kazutaka Kusano, "Hikari Shokubai o Riyo shita Zanryu Noyaku Keigen no Kanosei no Kento", Kanagawa-ken Nogyo Sogo Kenkyusho Shiken Kenkyu Seisekisho (Nogyo Kankyo), 2001, pp. 317-318. Cited in the int'l. search report.
Shinji Kato, Journal of the Society of Materials Science, Japan, vol. 51, No. 6, pp. 599-603, Jun. 15, 2002, Cited in the int'l. search report.
European Search Report dated Jun. 20, 2008, issued in corresponding European Patent Application No. 02 74 1304.

* cited by examiner

*Primary Examiner* — Brandon Fetterolf
*Assistant Examiner* — Paul Zarek
(74) *Attorney, Agent, or Firm* — Westerman, Hattori, Daniels & Adrian, LLP

(57) ABSTRACT

An agricultural chemical component includes an active agricultural chemical ingredient and a powder metal-modified apatite which has part of metal atoms in its apatite crystal structure provided by an optically catalytic metal. Preferably, the metal-modified apatite is coated with an organic film.

9 Claims, 3 Drawing Sheets

AGRICULTURAL CHEMICAL COMPONENT AND DECOMPOSER FOR RESIDUAL AGRICULTURAL CHEMICAL

This application is a continuation of international application PCT/JP02/06370 filed on Jun. 25, 2002.

TECHNICAL FIELD

The present invention relates to agricultural chemical components containing an ingredient for decomposing active agricultural chemical ingredients which are residual in the crops. The present invention also relates to decomposers for residual agricultural chemicals.

BACKGROUND ART

When growing agricultural crops, a variety of agricultural chemicals are sprayed sometimes, for disease prevention, pest control and increased yield. Most of the agricultural chemicals are organic chemical compounds which include, within their molecules, a specific chemical structure that determines their characteristic behaviors as the chemical. A large number of these agricultural chemicals are highly toxic not only to pest insects and viruses but also to human bodies. Further, agricultural chemicals have strong influences on the ecology in the agricultural fields and their surroundings, and potentially destructive to the ecology. For these reasons, the molecular structure of agricultural chemicals is designed so that the agricultural chemicals will decompose naturally with the elapse of time.

However, such a natural decomposition of agricultural chemicals is usually a slow process. Therefore, if there is only a short period of time between the high season of a pest and the harvesting season of an agricultural crop, most of the necessary amount of the agricultural chemical which is applied on time is not decomposed before the harvesting season, and the crop would have to be harvested with a large amount of the agricultural chemical still attached as residual agricultural chemical. In view of safety for human bodies and others, it is not preferable that agricultural crops are shipped with residual agricultural chemicals. In order to reduce the amount of residual agricultural chemicals at the time of harvest, sometimes the agricultural chemicals are applied before the pest season. However, natural decomposition of agricultural chemicals begins right after the application, so if the application is made earlier than the outbreak timing, necessary amount of the agricultural chemical will not be present at the outbreak of the pest nor during the time of spread thereafter. In this case, it is impossible to achieve satisfying effects with the agricultural chemical. As described, according to the conventional agricultural chemical technology, it is difficult to let agricultural chemicals exhibit satisfying effects and to reduce residual agricultural chemicals.

DISCLOSURE OF THE INVENTION

The present invention was made under the above-described circumstances, and it is therefore an object of the present invention to provide an agricultural chemical component capable of allowing the agricultural chemical to exhibit its effect appropriately while reducing residual agricultural chemical. Another object of the present invention is to provide a residual-agricultural-chemical decomposer.

A first aspect of the present invention provides an agricultural chemical component. The agricultural chemical component includes an active agricultural chemical ingredient and a powder metal-modified apatite in which part of metal atoms in its apatite crystal structure are provided by an optically catalytic metal. The optically catalytic metal atom is a metal atom which is capable of working as a center of optical catalyst in the form of oxide.

In the metal-modified apatite used in the present invention, the apatite which provides the basic structure can be expressed in the following general formula:

$$A_x(BO_y)_z X_s \qquad (1)$$

In the formula (1), the symbol A represents a metal such as Ca, Co, Ni, Cu, Al, La, Cr, Fe and Mg. The symbol B represents P, S and so on. The symbol X represents a hydroxyl (—OH), a halogen (e.g. F and Cl), and so on. More specifically, examples of the apatite which provides the basic structure of the metal-modified apatite include hydroxyapatite, fluoroapatite and chloroapatite. An apatite which can be used suitably in the present invention is a hydroxyapatite which is expressed in the above formula, with the symbol X provided by hydroxyl (—OH). More preferably, it is a calcium hydroxyapatite (Ca HAP), with the symbol A in the above formula provided by Calcium (Ca), the symbol B provided by phosphorus (P), and the symbol X provided by hydroxyl (—OH), i.e. $Ca_{10}(PO_4)_6(OH)_2$.

Calcium hydroxyapatite (Ca HAP) can exchange ions with both cations and anions, and therefore is highly adsorbent. In particular, it is superb in adsorbing organic matters. For this reason, Ca HAP has been a subject of research in applied technology in many different fields including chromatography adsorbent, chemical sensor, and ion exchanger. Also, Ca HAP is a principal ingredient of animal hard tissues such as teeth and bones. Chicken born dust which contains Ca HAP is widely used as a phosphorus fertilizer.

Examples of the optical catalytic metal atoms contained in the metal-modified apatite used in the present invention include titanium (Ti), zinc (Zn), tungsten (W), manganese (Mn), tin (Sn), indium (In) and iron (Fe).

Some oxides of these metals constitute metal oxide semiconductors, and are known to work as optical catalyst. Generally, in the semiconductor materials which work as optical catalyst, absorption of a light which has a level of energy equivalent to a band gap between the valence band and the conduction band causes transition of electrons from the valence band to the conduction band. Due to this transition of electrons, the valence band has electron holes. The electrons in the conduction band move to a matter adsorbed on the surface of the optically catalytic semiconductor, and this movement can chemically reduce the adsorbed matter. The electron holes in the valence band get electrons from the matter which is adsorbed on the surface of the optically catalytic semiconductor, and this behavior can oxidize the adsorbed matter.

In titanium oxide ($TiO_2$) which has the optical catalyst capability, the electrons which have moved to the conduction band reduce oxygen in the air, and produce supueroxide anion ($.O_2^-$). At the same time, the electron holes in the valence band oxidize water which is adsorbed on the surface of titanium oxide, to produce hydroxy radicals (.OH). Hydroxy radials are highly oxidative. Therefore, if the material which is adsorbed by the optical catalytic titanium oxide is an organic matter for instance, working of the hydroxy radicals may eventually decompose the organic matter into water and carbon dioxide.

Titanium oxide which is capable of promoting the oxidation-decomposition reaction, based on the optical catalytic function described as above, is used widely in antibacterial agent, sterilizers, antifouling agents, deodorants, and so on. It must be noted however, that titanium oxide itself is poor in adsorbing matters on its surface.

When atoms of such an optical catalytic metal, which work as optical catalyst in the form of oxide, are taken into the apatite crystal structure as part of the metal atoms which provide the crystal structure of the apatite expressed in the formula (1), there is formed an optical catalytic partial structure within the apatite crystal structure which has an optical catalyst capability. The optical catalytic partial structure is, more specifically, thought to be built with the atoms of the optical catalytic metal which are taken into the apatite crystal structure in place of the metal atoms A in the formula (1) and oxygen atoms in the formula (1), having an equivalent structure to a metal oxide which has an optical catalyst capability.

Metal-modified apatite which has the chemical structure as described exhibits more efficient decomposing capability in well-lighted environments due to its combined effect of a high level of adsorbing capability and a capability as an optical catalyst than optical catalysts provided by metal oxide semiconductors which are poor in adsorbing capability.

According to the agricultural chemical component offered by the first aspect of the present invention, it is possible to sufficiently reduce residual agricultural chemicals by effectively utilizing the decomposing capability of an optically catalytic metal-modified apatite. In the metal-modified apatite according to the present invention, there is a complex structure, of an atomic level, made of an apatite which has a superb ability to adsorb, and an optical catalyst as described earlier. Therefore, after application of an agricultural chemical component which includes an active agricultural chemical ingredient and the metal-modified apatite, to an agricultural crop at an appropriate timing, the metal-modified apatite exhibits highly efficient decomposing capability to the active agricultural chemical ingredient, under well-lighted conditions such as during the daytime, based on a high adsorbing capability and an optical catalytic capability, and thus works as a superb residual-agricultural-chemical decomposer. Decreasing the amount of residual agricultural chemicals is preferable particularly in food crops in view of safety to human bodies. By storing the agricultural chemical component in a light-blocking container, premature decomposition of the active agricultural chemical ingredient in the agricultural chemical can be avoided.

Meanwhile, JP-A-7-187933 discloses a technique for fabricating particles which contain a complex structure, of an atomic level, of highly absorbent calcium phosphate and antibacterial silver. The complex structure has an improved antibacterial efficiency provided by silver. However, silver does not have a decomposing capability based on an optical catalytic principle. Therefore, the complex particle cannot work as a residual-agricultural-chemical decomposer.

The agricultural chemical component according to the first aspect of the present invention is suitable for letting agricultural chemicals or active agricultural chemical ingredients exhibit their effects appropriately. When utilizing conventional agricultural chemical components, it is sometimes necessary to make application too earlier than the pest outbreak timing, in order to reduce the amount of residual agricultural chemicals. On the contrary, when utilizing the agricultural chemical components according to the present invention, application timing may not be as early as before, due to accelerated decomposition of the active agricultural chemical ingredient. For example, the agricultural chemical components according to the present invention can be applied at the outbreak timing of the pest insect even if there is only a short time period from the pest outbreak timing to the harvest time. In other words, the agricultural chemical component according to the present invention has a higher level of freedom in terms of application timing than conventional agricultural chemical components, and therefore is suitable in letting the active agricultural chemical ingredient exhibit its effects.

As described, use of the agricultural chemical component according to the first aspect of the present invention enables to sufficiently reduce the residual agricultural chemicals while letting the active agricultural chemical ingredient exhibit its effect appropriately.

In the first aspect of the present invention, preferably, the metal-modified apatite is coated with an organic film.

A second aspect of the present invention provides a residual-agricultural-chemical decomposer. The residual-agricultural-chemical decomposer includes: a powder metal-modified apatite in which part of metal atoms in its apatite crystal structure is provided by an optically catalytic metal; and an organic film coating the metal-modified apatite.

In the first and the second aspects of the present invention, preferably, the organic film is transmissive to light.

Preferably, the metal-modified apatite is a calcium hydroxyapatite in which part of its Ca is substituted with Ti.

Preferably, a rate of Ti to a total amount of Ca and Ti in the metal-modified apatite is 3-11 mol %.

Preferably, the metal-modified apatite is decomposable by a soil microorganism system.

Other objects, characteristics and advantages of the present invention will become clearer from the following description of embodiments to be made with reference to the attached drawings.

BEST MODE FOR CARRYING OUT THE INVENTION

An agricultural chemical component according to the present invention contains an active agricultural chemical ingredient and a residual-agricultural-chemical decomposer. In the present embodiment, the agricultural chemical component further contains a medium for appropriate dispersion and mixing of these components, and is stored in a light-blocking container.

The term active agricultural chemical ingredient used herein means an organic chemical used for preventing a disease of an agricultural crop or to control insect pest from an agricultural crop, and includes chemicals which have beneficial effect or activity in killing insects, killing fungus, controlling viruses, killing mites, killing weed and so on. Examples of such active agricultural chemical ingredients include fenitrothion, pyrimidifen, DDT, malathion, hexaconazole and proamatine. Also, the term agricultural crops means plants grown by human being, and include grains, fruits, vegetables, flowers, turf and so on.

The medium can be water for example, depending on the kind of chemical species of the agricultural chemical.

The residual-agricultural-chemical decomposer according to the present invention is a metal-modified apatite in which the apatite crystal structure has part of its metal atoms provided by an optically catalytic metal. The optically catalytic metal atom is a metal atom which is capable of working as a center of optical catalyst in the form of oxide. According to the present embodiment, the metal-modified apatite is Ti–Ca HAP in which part of Ca is substituted by Ti.

Figure 1:
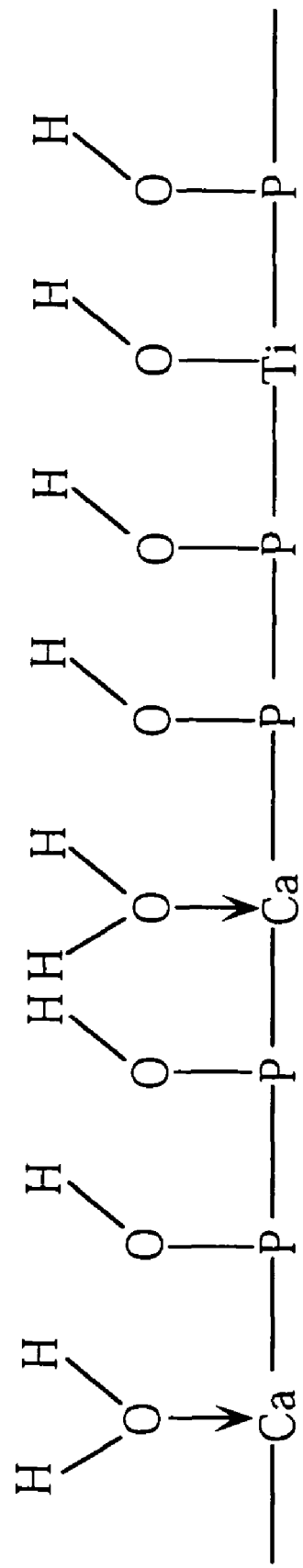
FIG. 1 shows a surface chemical structure model of a metal-modified apatite used in the present invention.

FIG. 1 shows a surface chemical structure model of Ti–Ca HAP. In the Ti–Ca HAP, inclusion of Ti provides an optical catalytic partial structure around the Ti within the apatite crystal structure. In such a Ti–Ca HAP, optical catalyst sites which have the optical catalytic partial structure and adsorbing sites which have a high capability to absorb a target matter for decomposition i.e. an active agricultural chemical ingredient scatter on the same crystal plane at an atomic scale. Therefore, Ti–Ca HAP has both of a high adsorbing capability and an optical catalyst capability, being able to decompose organic matters such as agricultural chemical components.

The metal-modified apatite should preferably contain the optically catalytic metal at a rate of 3-11 mol % with respect to a total metal content in its apatite crystal structure, in view of efficient improvement both in the adsorption by the metal-modified apatite and in the optical catalyst capability. Specifically, in Ti–Ca HAP, Ti/(Ti+Ca) should preferably have a value 0.03-0.11 (mol ratio). If the ratio is greater than 11 mol %, the crystal structure may be distorted. If the ratio is smaller than 3 mol %, there is an excess of the adsorbing sites, and too much of the adsorbed matter may not be processed sufficiently at too few optical catalyst sites, resulting in insufficient decomposition.

The agricultural chemical component according to the present embodiment contains, together with the active agricultural chemical ingredient, a powder of Ti–Ca HAP as described above, as the residual-agricultural-chemical decomposer. Thus, when the agricultural chemical component is applied to agricultural crops, Ti–Ca HAP attaches to the agricultural crops together with the active agricultural chemical ingredient. Thereafter, the active agricultural chemical ingredient exhibits an activity as an agricultural chemical while being decomposed in the natural process. In addition to this, the active agricultural chemical ingredient is also decomposed by the Ti–Ca HAP under sunlight during the day for example.

Specifically, under solar radiation, the titanium-oxide-like optical catalyst sites in the Ti–Ca HAP behave like titanium oxide, producing hydroxy radicals (.OH) from adsorbed water, whereas the adsorbing sites adsorb the active agricultural chemical ingredient. The adsorbed active agricultural chemical ingredient moves on the surface of Ti–Ca HAP due to surface diffusion, to or near the optical catalyst sites, where it is oxidized and decomposed by the hydroxy radicals.

In the Ti–Ca HAP where there is a complex structure, of an atomic level, made of an apatite which has a superb ability to adsorb and an optical catalyst, active agricultural chemical ingredients are decomposed efficiently under solar radiation, based on the high level of adsorbent and optical catalytic capability as described above. In other words, a net rate of decomposition of the active agricultural chemical ingredients is greater than a rate of purely natural decomposition. Thus, it becomes possible to reduce residual active agricultural chemical ingredients at the time of harvest even if there is only a short period of time between the time of pest season or the time of application of the agricultural chemical component and the time when the agricultural crop is harvested.

When using the agricultural chemical component according to the present embodiment, it is not necessary to apply the agricultural chemical component too earlier than the pest season in an attempt to reduce residual agricultural chemical, since the active agricultural chemical ingredient is decomposed at an increased rate. For example, the agricultural chemical component can be applied at the time of pest season even if there is only a short time period from the pest season to the time of harvest. In other words, the agricultural chemical component according to the present invention has a higher level of freedom in terms of application timing than conventional agricultural chemical components, and therefore more suitable in letting the active agricultural chemical ingredient exhibit its effect.

Ti–Ca HAP has a basic structure similar to the structure of Ca HAP. Therefore, once having decomposed the residual agricultural chemicals, Ti–Ca HAP may be washed into soil by rain for example, and then can be decomposed by bacteria and other microorganisms living in the soil. For this reason, multiple use of the agricultural chemical component according to the present embodiment in the same farm land will not cause eventual accumulation of the residual-agricultural-chemical decomposer. Further, since Ti–Ca HAP contains phosphorus acid and calcium, it works as a phosphorus fertilizer and a calcium fertilizer as it is decomposed. On the contrary, the optically catalytic titanium oxide is not decomposed by the soil system. Therefore, multiple use of an agricultural chemical component containing optically catalytic titanium oxide as a residual agricultural chemical component in the same farm land can result in an accumulation of the residual-agricultural-chemical decomposer in the soil, causing an adverse influence on the soil ecosystem.

According to the present invention, Ti–Ca HAP may be coated with an organic film. In such an arrangement, where the coating is present, what is subjected to the decomposition under solar radiation is the organic coating itself. Therefore, decomposition of the active agricultural chemical ingredient by Ti–Ca HAP is hindered at the place covered with the coating, and as a result, the net rate of decomposition of the active agricultural chemical ingredient by Ti–Ca HAP is low for a desired period of time, i.e. for a period of time until the organic film has been decomposed and disappeared to an adequate level.

Such an organic coating may be formed of e.g. gelatin, agar, natural and synthetic resins. The coating should have a thickness of 0.1-1 μm. Such an organic coating can be formed by first soaking a powder of Ti–Ca HAP into an organic solvent which contains an organic material for the organic coating, thereby having Ti–Ca HAP particles adsorb the organic material. Once the Ti–Ca HAP particles have adsorbed the organic material, the Ti–Ca HAP powder is taken out of the solvent, and dried. Alternatively, the solvent may be evaporated while containing the Ti–Ca HAP powder. By appropriately controlling the thickness of the organic coating thus made, it is possible to control the period of time in which there is a reduced rate of decomposition of active agricultural chemical ingredients by Ti–Ca HAP, by way of the amount of decomposition of the organic coating and transmissivity of light.

By providing the above-described period in which the net rate of decomposition of the active agricultural chemical ingredient by the metal-modified apatite is reduced, it becomes possible to sufficiently benefit from the active agricultural chemical ingredient during this period. In other words, it becomes possible to effectively use the agricultural chemical component.

Figure 2:
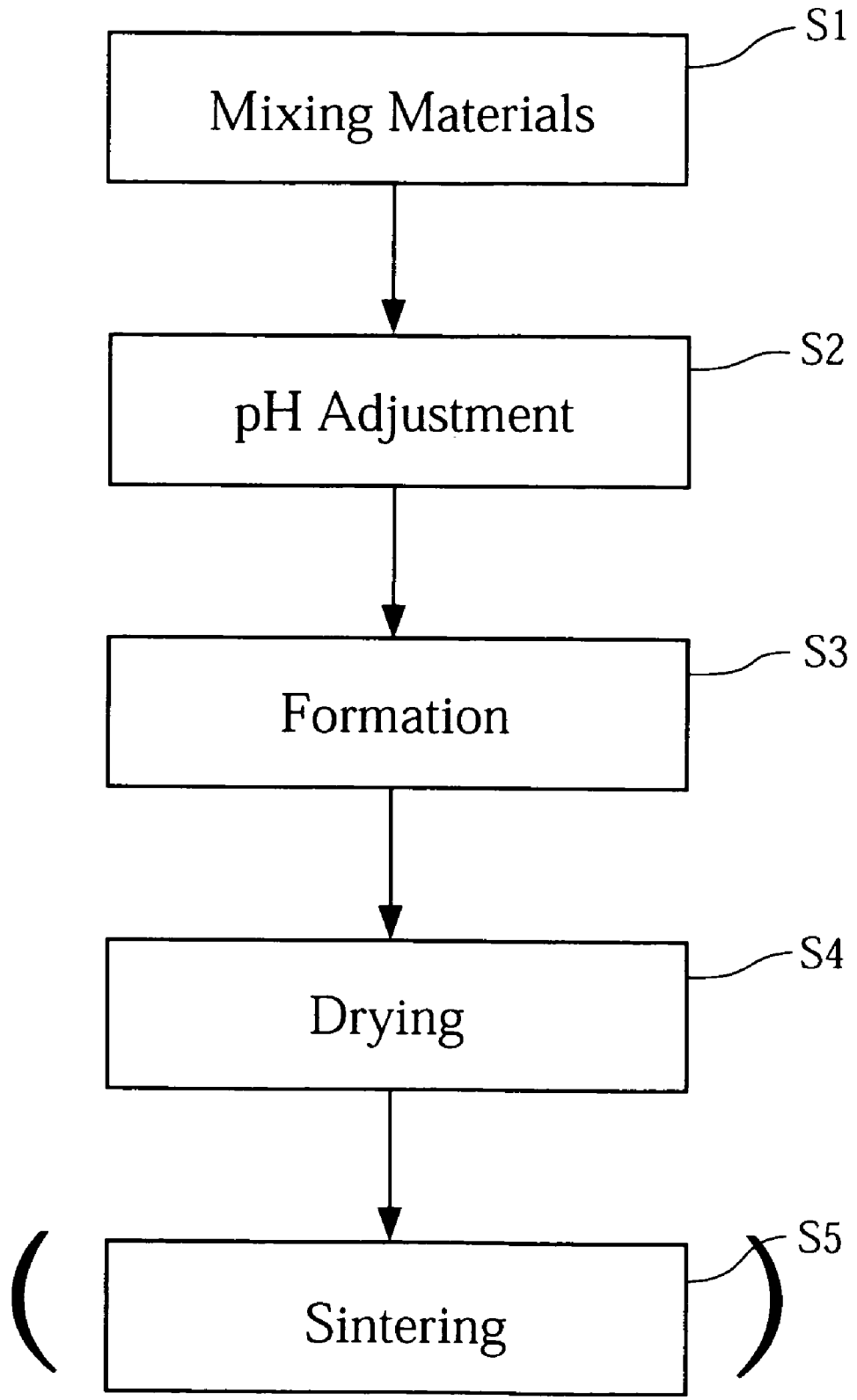
FIG. 2 is a flowchart of a method of fabrication of the metal-modified apatite used in the present invention.

FIG. 2 is a flowchart of a fabrication of the metal-modified apatite according to the present invention. In the fabrication of the metal-modified apatite, first, in a raw material mixing step S1, raw materials for forming the metal-modified apatite are mixed. For example, chemical species representing the symbols A, $BO_y$, and X in the formula (1) described earlier are added to a single aqueous solution, by respective predetermined amounts, and then mixed. If the metal-modified apatite which is supposed to be formed is Ti–Ca HAP, calcium nitrate for example can be used as a Ca supplier. Phosphoric acid for example can be a $PO_4$ supplier. Hydroxyls are supplied from aqueous solution of alkalis such as aqueous solution of ammonia, aqueous solution of calcium hydroxide or sodium hydroxide, which will be used in a step of pH adjustment to be described later. The optically catalytic metal or Ti can be supplied from titanium chloride or titanium sulfide.

The rate of the optically catalytic metal to a total metal content in the apatite crystal structure should preferably be in the range of 3-11 mol % as mentioned earlier. Therefore, in the material mixing step S1, it is preferable that the supply amount is determined for each of the raw materials, and adjustments are made to relative physical quantities to be supplied, so that the rate of the optical catalytic metal to a total metal content in the apatite crystal structure will become 3-11 mol %.

Next, in a pH adjustment step S2, the raw material solution which has been prepared as the above is adjusted to a specific pH at which formation of the target metal-modified apatite commences. The pH adjustment can be made by using aqueous solution of ammonia, aqueous solution of calcium hydroxide, aqueous solution of sodium hydroxide and so on. When forming e.g. Ti–Ca HAP as the metal-modified apatite, the raw material solution should preferably be adjusted to a value in a range of pH 8-10.

Next, in a formation step S3, formation of the metal-modified apatite is promoted, whereby crystallization of the target metal-modified apatite is promoted. Specifically, for example, after coprecipitating the apatite components and part of the optically catalytic metal in the raw material solution, the solution is aged at 100° C. for six hours, to obtain highly crystallized optical catalytic metal. When fabricating Ti–Ca HAP for example, the coprecipitatation process in this step allows Ti ions to be taken into Ca positions in the apatite crystal structure, allowing Ti–Ca HAP to grow.

Next, in a drying step S4, the metal-modified apatite which has been formed in the previous step is dried. Specifically, the powder of metal-modified apatite which has been separated in the formation step S3 is filtered, and then the sediment which has been filtered out is cleaned in pure water, and then dried. The drying temperature should preferably be 100-200° C. This step removes liquid components in the raw material solution from the metal-modified apatite.

The powder metal-modified apatite thus fabricated undergoes a sintering step S5 as necessary. In the sintering step S5, the metal-modified apatite is heated again, separately from heating in the drying step S4, whereby the metal-modified apatite is sintered. The sintering temperature should preferably be 580-660° C. In the case of Ti–Ca HAP for example, this sintering step improves optical catalyst activity.

Next, examples of the present invention will be described together with comparative examples.

Example 1

<Fabrication of a Residual-Agricultural-Chemical Decomposer>

In the present Example, Ti–Ca HAP was made as the metal-modified apatite which serves as a residual-agricultural-chemical decomposer. In the fabrication of Ti–Ca HAP, a liter of decarbonated pure water was prepared. To this pure water, calcium nitrate, titanium sulfide and phosphoric acid were added and mixed in nitrogen atmosphere. The concentration of calcium nitrate was adjusted to 0.09 mol/L, the concentration of titanium sulfite was adjusted to 0.01 mol/L whereas the concentration of phosphoric acid was adjusted to 0.06 mol/L. Next, the pH of the raw material solution was adjusted to 9.0 by adding ammonia water of the 15 mol/L. Next, the raw material solution was aged at 100° C. for six hours. Through these operations, the metal-modified apatite occurred and precipitated in the raw material solution, and the raw material solution became a suspension. The suspension was filtered, and the separated deposit was cleaned with five liters of pure water, and then dried in a dry oven at 70° C. for 12 hours, to obtain Ti–Ca HAP which has an average size of 0.05 µm per grain. This Ti–Ca HAP had an abundance ratio between Ti and Ca, which was Ti:Ca=1:9. In other words, the abundance ratio of Ti, which serves as the catalyst metal atoms, to a total amount of metal atoms contained in the metal-modified apatite crystal structure was 10 mol %. The abundance ratio of Ti to Ca was determined on the basis of quantitative analysis using ICP-AES (Plasma Emission Spectrometry).

<Preparation of an Agricultural Chemical Component>

An agricultural chemical solution (Brand name: Sumithion, manufactured by Takeda Engei Co., Ltd.) which contains fenitrothion as an active agricultural chemical ingredient was diluted with water to 1000 times. To the diluted solution, the Ti–Ca HAP powder obtained as the above was mixed at a rate of 10 wt %, to obtain an agricultural chemical component according to the present example.

<Decomposition Test of the Residual Agricultural Chemical>

Decomposition of residual agricultural chemical component contained in the agricultural chemical component prepared as the above was examined. Specifically, first, the agricultural chemical component was applied, by means of spin coating, on a glass plate which had a size of 50 mm×50 mm. Next, a plurality of the glass plates thus coated with the agricultural chemical component were left in an outdoor environment for four weeks. At every half a week starting from the exposure, the active agricultural chemical ingredient was extracted from a predetermined amount of area on the glass plates, and an amount of residual agricultural chemical component was measured to see the rate of residual active agricultural chemical ingredient to the original amount. The measurement or quantification of the active agricultural chemical ingredient was made in two different methods, i.e. gas chromatography and mass spectroscopy. Results were plotted in Graph A1 in FIG. 3, with the horizontal axis representing time of exposure and the vertical axis representing the rate of residual active agricultural chemical ingredient.

Example 2

In the present Example, a residual-agricultural-chemical decomposer was prepared by coating the same Ti–Ca HAP powder as in Example 1 with gelatin. Specifically, first, gelatin was dissolved into water which has been heated to above 50° C., so that the final concentration would be 0.1 g/L. Next, the same Ti–Ca HAP powder as in Example 1 was added to the solution, and mixed for an hour under heating, thereby having Ti–Ca HAP particles adsorb the gelatin. Next, the Ti–Ca HAP was separated by filtration, and dried to obtain Ti–Ca HAP powder coated with a 0.1-µm gelatin film. A residual-agricultural-chemical decomposer according to the present Example was thus fabricated. An agricultural chemical solution (Brand name: Sumithion, manufactured by Takeda Engei Co., Ltd.) which contains fenitrothion as an active agricultural chemical ingredient was diluted with water to 1000 times. To the diluted solution, the Ti–Ca HAP powder obtained as the above was mixed at a rate of 10 wt %, to obtain an agricultural chemical component according to the present example. The same residual agricultural chemical decomposition test was conducted by using the agricultural chemical component according to the present example, to obtain Graph A2 in FIG. 3.

Comparative Example 1

An agricultural chemical solution (Brand name: Sumithion, manufactured by Takeda Engei Co., Ltd.) which contains fenitrothion as an active agricultural chemical ingredient was diluted with water to 1000 times, to prepare an agricultural chemical component according to the present example, and the same residual agricultural chemical decomposition test was conducted by using the agricultural chemical component according to the present example, to obtain Graph B1 in FIG. 3.

Evaluation

Figure 3:
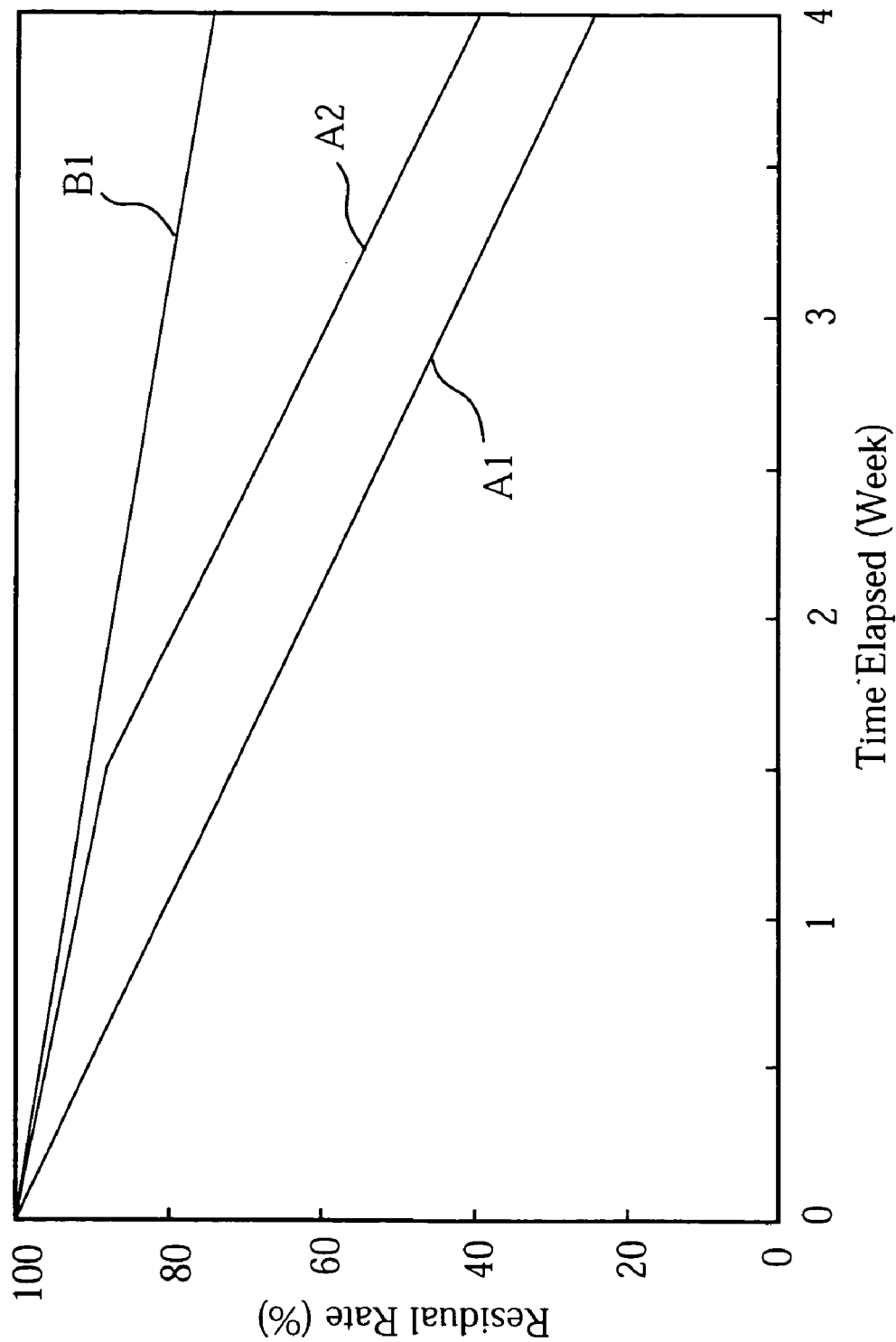
FIG. 3 is a graph showing how a rate of residual agricultural chemical changed in Examples 1 and 2 as well as in Comparative Example 1.

Referring to FIG. 3, it is understood that the active agricultural chemical ingredient used in the present examples and the comparative example decomposes naturally at a slow rate as shown in Graph B1. By comparing Graph A1 and Graph B1, it will be understood that the active agricultural chemical ingredient decomposes more quickly than in the natural decomposition process if it contains an optically-catalytic metal-modified apatite or Ti–Ca HAP. The decomposition speed in Example 1 is about three times the decomposition speed in Comparative Example 1. Further, by comparing Graph A1 and Graph A2, it will be understood that decomposition of the active agricultural chemical ingredient is slowed for a period of time and then promoted if the active agricultural chemical ingredient has its particles coated with an organic film or gelatin.

The invention claimed is:

1. An agricultural chemical mixture comprising:
   an active agricultural chemical ingredient for an agricultural purpose; and
   a powder metal-modified apatite mixed with the active agricultural chemical ingredient for application together with the active agricultural chemical ingredient for decomposing the active agricultural chemical ingredient, the powder metal-modified apatite having part of metal atoms in its apatite crystal structure provided by an optically catalytic metal.

2. The agricultural chemical mixture according to claim 1, wherein the metal-modified apatite alone is coated with an organic film.

3. The agricultural chemical mixture according to claim 2, wherein the organic film is transmissive to light.

4. The agricultural chemical mixture according to claim 1, wherein the metal-modified apatite is a calcium hydroxyapatite having part of its Ca substituted with Ti.

5. The agricultural chemical mixture according to claim 4, wherein a rate of Ti to a total amount of Ca and Ti in the metal-modified apatite is 3-11 mol %.

6. A residual-agricultural-chemical decomposer for mixture with an active agricultural chemical ingredient, comprising:
   a powder metal-modified apatite having part of metal atoms in its apatite crystal structure provided by an optically catalytic metal; and
   an organic film coating only the metal-modified apatite.

7. The residual-agricultural-chemical decomposer according to claim 6, wherein the organic film is transmissive to light.

8. The residual-agricultural-chemical decomposer according to claim 6, wherein the metal-modified apatite is a calcium hydroxyapatite having part of its Ca substituted with Ti.

9. The residual-agricultural-chemical decomposer according to claim 6, wherein a rate of Ti to a total amount of Ca and Ti in the metal-modified apatite is 3-11 mol %.

* * * * *